United States Patent
Byrne et al.

(10) Patent No.: US 7,150,054 B1
(45) Date of Patent: Dec. 19, 2006

(54) SAFETY APPARATUS AND METHOD OF USE

(75) Inventors: Richard Byrne, Doncaster (GB); Carol A. Betz, Carson City, NV (US); Nicola D. Pieters, Carson City, NV (US)

(73) Assignee: Mommy's Little Helpers, LLC, Carson City, NV (US)

( * ) Notice: Subject to any disclaimer, the term of this patent is extended or adjusted under 35 U.S.C. 154(b) by 0 days.

(21) Appl. No.: 11/233,675

(22) Filed: Sep. 22, 2005

Related U.S. Application Data

(60) Provisional application No. 60/719,671, filed on Sep. 21, 2005.

(51) Int. Cl.
*A47D 15/02* (2006.01)
*A47G 9/02* (2006.01)

(52) U.S. Cl. ............................... 5/494; 5/655; 128/872
(58) Field of Classification Search ............... 5/485, 5/494, 496, 498, 655, 923; 128/872, 873
See application file for complete search history.

(56) References Cited

U.S. PATENT DOCUMENTS

| 857,507 | A | | 6/1907 | Wilson | |
|---|---|---|---|---|---|
| 1,678,125 | A | | 7/1928 | Petrescu | |
| 1,863,256 | A | | 6/1932 | Snoddy | |
| 1,964,271 | A | | 6/1934 | O'Dwyer | |
| 2,313,337 | A | * | 3/1943 | Gurke | 128/872 |
| 2,643,396 | A | * | 6/1953 | Routman | 5/494 |
| 2,850,746 | A | * | 9/1958 | Foehner | 5/494 |
| 3,845,513 | A | | 11/1974 | Hubner | |
| 4,202,052 | A | | 5/1980 | Bilanzich | |
| 4,653,131 | A | | 3/1987 | Diehl | |
| 4,993,090 | A | * | 2/1991 | Ranalli | 5/482 |
| 5,233,714 | A | | 8/1993 | De Bell Daniel | |
| 5,400,803 | A | | 3/1995 | Vines | |
| 5,746,219 | A | | 5/1998 | McConnell | |
| 5,933,886 | A | | 8/1999 | Washington | |
| 5,950,261 | A | * | 9/1999 | Hay et al. | 5/482 |
| 6,095,614 | A | * | 8/2000 | Canna et al. | 297/468 |
| 6,301,729 | B1 | | 10/2001 | Hall | |
| 6,381,785 | B1 | | 5/2002 | Mancera Browne et al. | |
| 6,457,193 | B1 | | 10/2002 | Li | |
| 6,662,390 | B1 | | 12/2003 | Berger | |
| 6,681,422 | B1 | | 1/2004 | Landry | |
| 6,708,356 | B1 | * | 3/2004 | LaValle | 5/655 |
| 6,834,405 | B1 | * | 12/2004 | Hillstead | 5/655 |

(Continued)

*Primary Examiner*—Michael Trettel
(74) *Attorney, Agent, or Firm*—Klarquist Sparkman, LLP

(57) ABSTRACT

Body orienting harnesses and associated structures are disclosed, along with methods of use. The body orienting harness can position a body, such an infant, with respect to the associated structure, such as a bed, bed frame or crib, a sheet, or a blanket for example. The harness may be integrated with a sheet or blanket in order to secure not only a body in position but also secure the sheet or blanket in position with respect to the body. The sheet, blanket, or other cover, can provide a slip cover for an underlying support surface, such as a mattress for example. Alternatively, the cover can be secured in other ways to form a pocket in association with other structure, such as a bed sheet for example. The harness can be mounted in association with the pocket to secure a body in position with the respect to the pocket and associated structure, such as a mattress, crib, etc. When used to secure an infant during sleep, certain embodiments of the harness and associated structure can help significantly reduce the chance of overheating, suffocating, or otherwise harming the infant.

22 Claims, 5 Drawing Sheets

U.S. PATENT DOCUMENTS 6,848,131 B1   2/2005   Landry
6,857,146 B1   2/2005   Landry
6,868,566 B1   3/2005   Gatten
7,076,819 B1   7/2006   Trani et al.

* cited by examiner

SAFETY APPARATUS AND METHOD OF USE

CROSS REFERENCE TO RELATED APPLICATION

This application claims the benefit of, and incorporates herein by reference in its entirety, the applicants' prior U.S. provisional patent application 60/719,671 of the same title, Safety Apparatus and Method of Use, filed Sep. 21, 2005, Express Mail Label No. ED 636571765US.

FIELD

This application concerns a device for orienting a body with respect to another object and method of use. In one embodiment, the application concerns a device for relatively securely orienting a human body, such as a sleeping infant for example, with respect to an adjacent blanket or sheet and method of use.

BACKGROUND

A common problem faced by caregivers and parents of an infant, particularly a young infant, is that the infant typically is unable to keep a blanket over a lower portion of the infant while the infant is asleep. This arises because the infant may move around during sleep or kick off the blanket. This can result in the infant becoming cold during sleep and therefore waking, requiring the attention of an adult to re-cover the infant. In more serious cases, the blanket can be moved up over the face of the infant or the infant may slip down under the blanket thus increasing the risk of overheating and suffocation of the infant.

A further problem commonly faced by caregivers and parents of infants is that the infant may roll over onto its stomach during sleep thus also increasing the risk of suffocation. Also, the infant may roll over during sleep and wedge their face against the side of a cot in which it sleeps, again increasing the risk of suffocation.

Yet another problem for caregivers and parents is the possible loss of oxygen and other problems (such as falling out of bed) that may arise for an infant if it moves toward the sides or headboard of bed.

One solution known in the art is to tuck a blanket tightly around an infant and hope that the infant does not have enough strength to remove the blanket. However, there is a risk that the blanket could be tucked too tight and thus restrict the infant's breathing. A further known solution is to simply not cover the infant during sleep, but provide a very warm room in which the infant can sleep. However, the cost of heating a room to a suitable temperature, and maintaining the same, renders such a solution impractical to most parents. Also, the use of heaters to maintain such a temperature increases the risk of fire thus endangering the infant.

SUMMARY

Certain embodiments of the present invention address one or more of the above mentioned problems and provide a solution which reduces the risk of suffocation to an infant while also reducing the infant's discomfort.

Some embodiments provide a safety device for offering increased safety to a sleeping infant comprising cover means operable to cover at least a portion of an infant and securing means operable to secure at least a portion of an infant to the cover means.

In certain embodiments, the cover means comprise a blanket or sheet. The cover means may be formed of a soft material which may be a fabric material. The cover means may be formed from any natural or synthetic fabric, or any woven or non-woven fabric. Examples of a soft fabric material include brushed cotton and fleece.

In certain embodiments, the securing means are adjustable. The securing means may comprise a support member that may be adapted to fit between the legs of an infant. The support member may comprise a seat that is preferably adapted to support the seat of an infant. The support member may be attached to a first face of the sheet, such as, for example, toward a first end thereof. The support member may comprise a crotch strap or support.

In some embodiments, the securing means comprises strapping means, which strapping means may be adapted to strap an infant to the cover means. The strapping means may comprise a strap, a center section of which may be attached toward a second end of the support member. The securing means can generally triangularly or T-shaped. The securing means may comprise a harness that may fit between an infant's legs and around an infant's waist or torso.

The cover means may comprise at least one aperture. Alternatively, the cover means may comprise at least two apertures. The strapping means may be adapted to pass through the at least one aperture in the cover means. The strapping means can be adapted to pass through the at least two apertures in the cover means.

In some embodiments, the securing means is operable to secure at least a portion of an infant to a first face of the cover means. The securing means can be operable to be adjusted at a second face of the cover means.

The safety device may also further comprise strap retaining means operable to secure the strapping means to the cover means. The strap retaining means can be attached to the second face of the cover means.

In certain embodiments, toward a first end of the strapping means are attachment means operable to removably attach the first end of the strapping means to the strap retaining means. Toward a first end of the strapping means may be strap attachment means operable to removably attach a second end of the strapping means thereto. In addition, toward a second end of the strapping means may be attachment means operable to removably attach the second end of the strapping means to the first end of the strapping means.

In certain embodiments, the safety device is adapted to be attached to or incorporated within a surface, which surface may be substantially planar. In certain embodiments, the surface is a surface upon which an infant sleeps. Alternatively, the safety device may be sized and used with other than infants, in order to more reliably secure a non-infant in position, such as infirm elderly person.

The safety device may be attached to or incorporated within a bed sheet or mattress such that an infant (or other body) may be held in position relative to the bed sheet or mattress by the safety device. The safety device can be attached to or incorporated within a bed sheet or mattress so as to form a pocket. The pocket can be adapted to receive an infant therein and may be locate to maintain the infant in a desired position with respect to the bed or other structure, including the bed sheet.

In some embodiments, the support member is attached to an internal face of the cover means when the safety device is attached to or incorporated within a bed sheet or mattress. By internal face of the cover means it is meant a face of the cover means which directly abuts the mattress or bed sheet. The strapping means may be operable to be secured to an external face of the cover means when the safety device is attached to a mattress or bed sheet (and in this application, the term "sheet" includes blankets as well as conventional bed sheets).

In certain embodiments, a method of securing an infant (or other body) to a surface comprises the steps of: attaching a safety device comprising cover means and securing means to a surface, placing an infant or other body between the safety device and the surface, adjusting the securing means to fit the infant or other body, and securing the infant or other body to the safety device using the securing means. The method may instead or in addition comprise placing a cover on the infant or other body after first placing the infant or other body in the security means, such as a harness, and securing the harness in place. Other methods are disclosed.

In certain embodiments, the surface is a mattress or bed sheet.

All of the above aspects may be combined with any of the features disclosed herein in any combination.

The foregoing is a brief summary of aspects of the various embodiments disclosed in this specification. There are additional aspects that will become apparent as this specification proceeds. In addition, it is to be understood that embodiments of the invention need not include all such aspects or address all issues in the Background above.

BRIEF DESCRIPTION OF THE DRAWINGS

The preferred and other embodiments are shown in the accompanying drawing in which.

In the following Detailed Description section various spacially orienting terms are used such as "upper" and "lower." It is to be understood that such terms are used for convenience in association with the drawings but are not be themselves limiting or requiring of any absolute orientation in space.

DETAILED DESCRIPTION OF PREFERRED EMBODIMENTS

Figure 1:
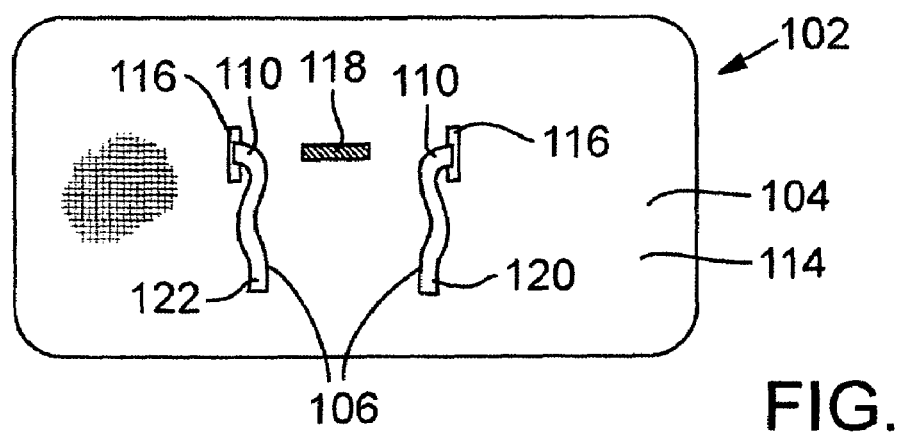
FIG. 1 shows a perspective view of a front surface of a safety (or securing) device.
Figure 2:
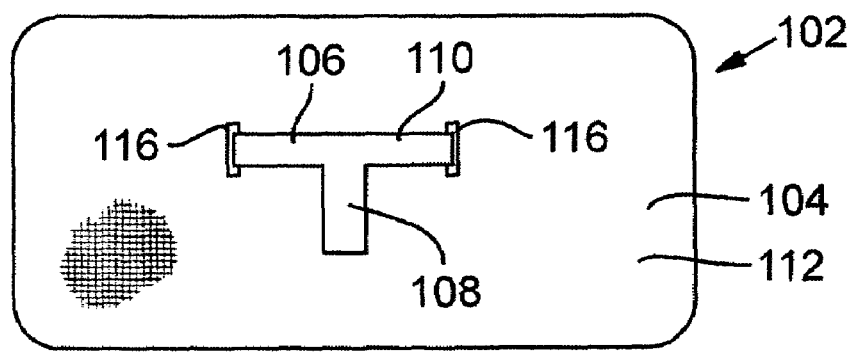
FIG. 2 shows a perspective view of a rear surface of a safety device.

Referring to FIGS. 1 and 2, a safety device 102 comprises cover means in the form of a rectangular sheet 104, and a harness 106. The sheet 104 and the harness 106 are formed of a flexible, soft, and breathable material, such as fleece. It should be appreciated that the sheet 104 and the harness 106 may be made from any suitable material. Factors to consider when choosing a suitable material include the softness of the material, possible irritation to the infant's skin, climate in which the device will be used (i.e., cooling fabrics for warmer climates, etc.) fabrics which will not react to an infant's bodily excretions such as saliva, vomit and urine, etc.

The harness 106 comprises a gusset strap 108 as displayed in FIG. 2 and a securing strap 110 extending perpendicularly away from each side of a first end thereof. The gusset strap 108 of the harness 106 is attached at a second end thereof to a rear face 112 of the sheet 104. The attachment may be accomplished in a wide variety of ways, such as by stitching or with buttons in mating button holes in the harness, or via other fastening techniques.

The opposing ends of the securing strap 110 pass from the rear face 112 of the sheet 104 to a front face 114 of the sheet 104 via two laterally spaced elongate apertures 116 in the sheet 104. Therefore, as shown in FIG. 2, the harness 106 forms a T shape, but other shapes may be utilized.

Figure 6:
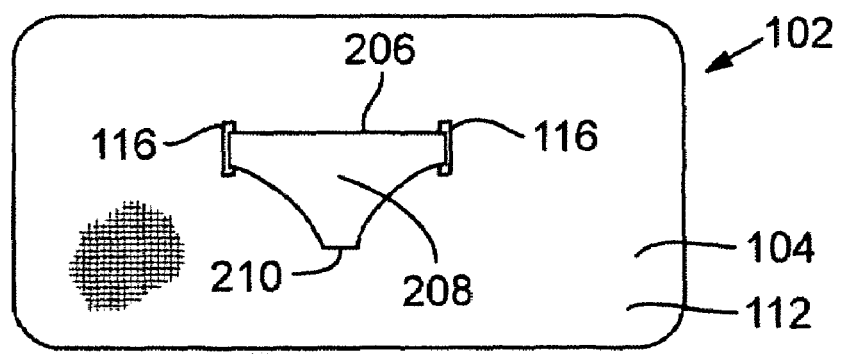
FIG. 6 shows a perspective view of a rear surface of a second embodiment of a safety device.

An alternative embodiment of a harness 206 is shown in FIG. 6. In this embodiment, the harness 206 has a seat 208 of a shape that an infant can sit in, for example, in the shape of a seat of a pair of briefs. A bottom edge 210 of the seat 208 is secured to the rear face 112 of the sheet 104. Attached at opposing sides toward the top of the seat 208 are securing straps (not shown) which extend through the apertures 116 and function in the same manner as will be described below. The front face 114 of the sheet 104 fitted with the preferred harness 206 is as described with reference to FIG. 1 below.

The front face 114 of the sheet 104 (as shown in FIG. 1) has a securing pad 118 approximately centrally disposed between the two apertures 116. The securing pad 118 is attached to the sheet 104 by stitching and has female hook and pile fastener on its outer surface, e.g., the pile portion of the hook and pile fastener.

Toward a first end 120 of the securing strap 110 there is attached a portion of hook and pile fastener on each face thereof (not shown), one portion being male hook and pile fastener, the other portion being female hook and pile fastener. Toward a second end 122 of the securing strap there is attached a portion of male hook and pile fastener (not shown).

It is preferred that the male hook and pile fastener (i.e., the hook portion) be attached on the surfaces which are least likely to come into contact with an infant, in use. This is because the texture of the male hook and pile fastener is coarse and may irritate an infant, whereas the female hook and pile fastener (the pile) has a softer texture. This is exemplified by providing the female hock and pile fastener on the securing pad 118 which faces upwards, away from the infant, in use.

The device 102 may be attached to or form part of a mattress or cushion upon which an infant sleeps.

Figure 4:
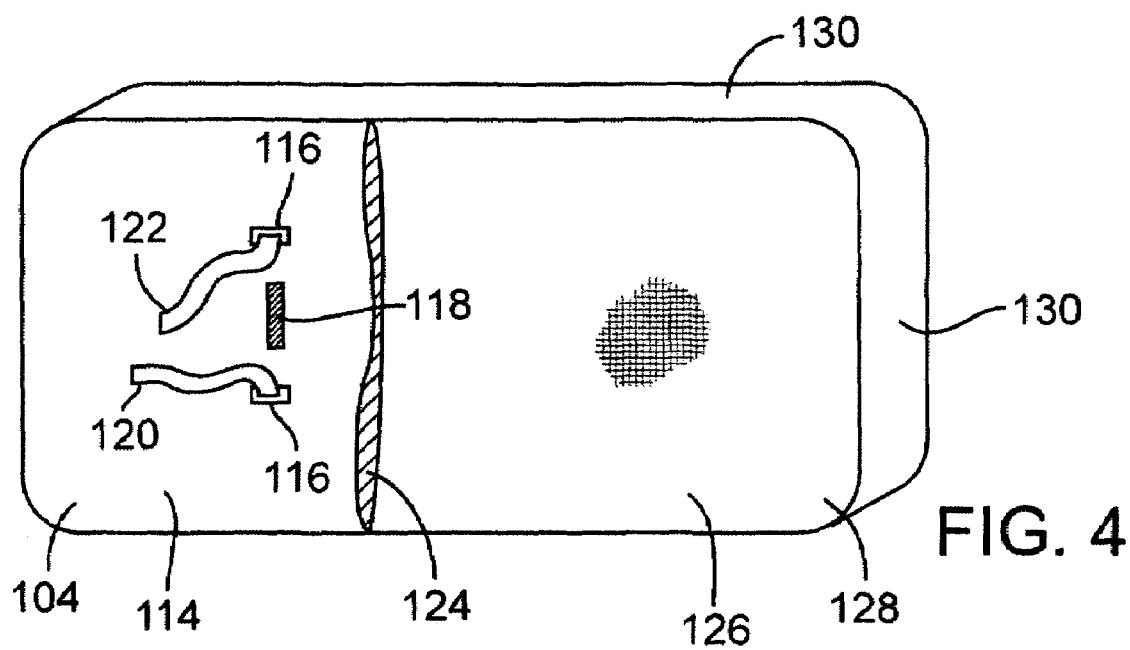
FIG. 4 shows a perspective view of a safety device attached to a fitted bed sheet in a predetermined position (for example to secure an infant adjacent the foot of a bed or at least away from the head or head board of a bed)
Figure 5:
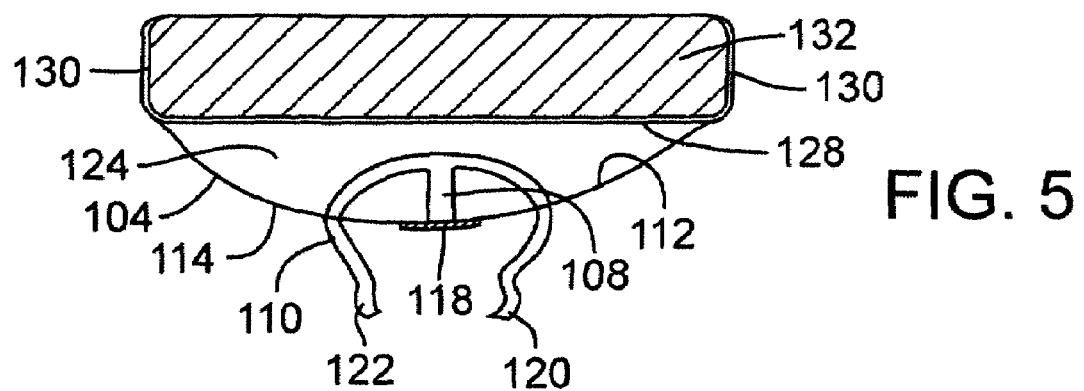
FIG. 5 shows a partial cross-sectional view from the top of a safety device attached to a bed sheet, the bed sheet being fitted to a mattress.

Alternatively, as shown in FIGS. 4 and 5, the device 102 may be attached to or form part of a fitted bed sheet 126. In this embodiment, a fitted bed sheet has an upper face 128 and side faces 130 of an appropriate size to fit an infant's mattress 132. The device 102 may be attached to the upper face 128 of the fitted bed sheet 126.

Figure 3:
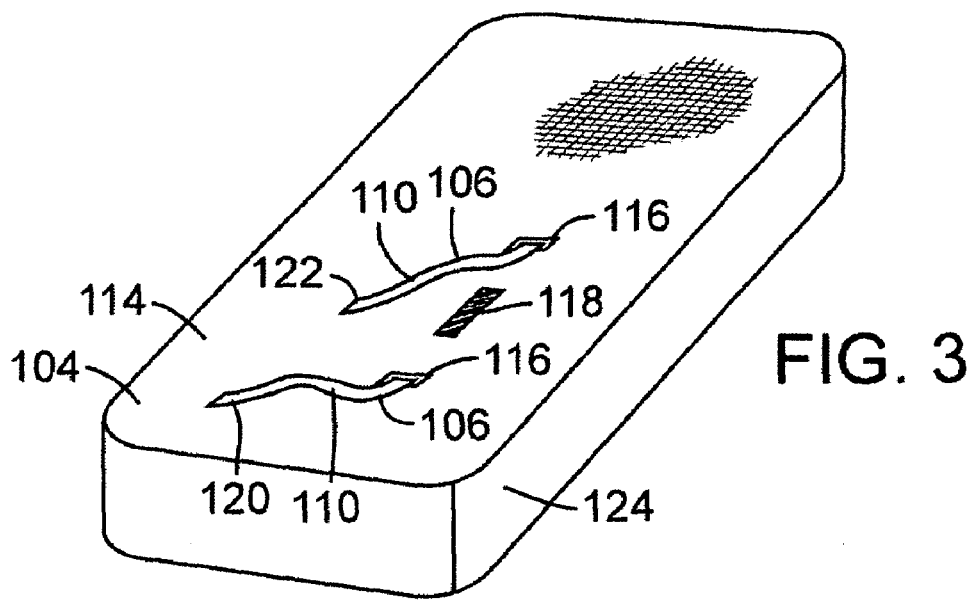
FIG. 3 shows a perspective view of a safety device attached to a mattress cap.

The attachment or incorporation of the device 202 onto or into a bed sheet, mattress, cushion etc. should incorporate a pocket 124 as shown in FIGS. 3, 4 and 5 into which an infant may be placed.

A further alternative (shown in FIG. 3) is to form the sheet 104 into a pocket which may be fitted over one end of a mattress already fitted with a bed sheet. The device 102 would therefore be held in place by the weight of the mattress.

The sheet 104 is shown in a preferred rectangular shape, however it should be appreciated that many shapes of sheet could perform the same function in a similar manner.

In use, an infant (not shown) is placed under the sheet 104 such that the gusset strap 108 of the harness 106 sits between the infant's legs and the securing strap 110 around the infant's waist or torso. The ends of the securing strap 110 are then pulled through the apertures 116 so that the infant is pulled toward the rear face 112 of the sheet 104. The first end 120 of the securing strap 110 is then attached to the securing pad 118 by the hook and pile fastener thereon. The second end 122 of the securing strap 110 is then attached to the first end 120 of the securing strap 110 by the hook and pile fastener between them.

Figure 7:
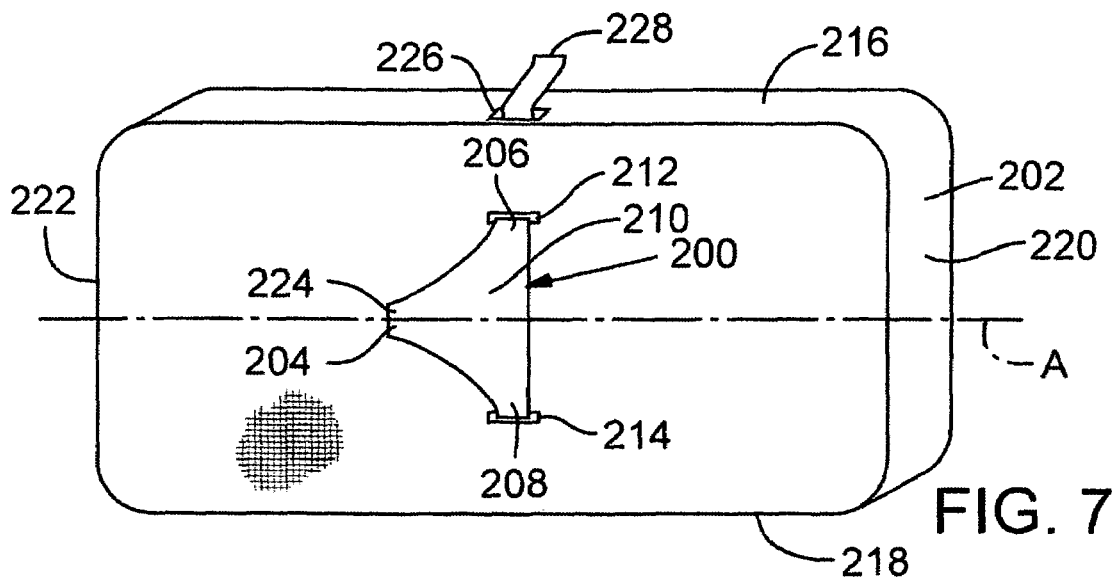
FIG. 7 shows a perspective view of a safety device secured to a fitted mattress with straps penetrating passages in the fitted sheet.

As shown in FIG. 7, yet another embodiment of the safety or securing device has a harness 200 that is mountable to fitted or other sheet 202, which is in turn mounted to a bed mattress (not shown). In this embodiment, the harness 200 has a generally semi-triangular or T-shape with three securing straps 204, 206, 208 extending from the central body 210 of the harness 200. Two collinear but opposing securing straps 206, 208 penetrate mating securing strap passages, 212, 214 respectively, in the sheet 202. The mating securing strap passages 212, 214 are equidistant from the axial center A of the bed mattress, in order to center a body secured by the harness 200 in the axial center of the bed mattress and equally spaced from the opposing lateral sides 216, 218 and top and bottom sides 220, 222 of the sheet on the bed mattress.

A center, axially extending securing strap 204 extends from the central body 210 transverse to the opposing securing straps 206, 208 toward the bottom or foot of the bed 222. The remote end 224 of the axially extending strap 204 is secured to the bed sheet 220 such as by stitching or other fastening means.

Each of the opposing securing straps, e.g., 204, extends from its mating securing strap passage, e.g., 212, between the sheet 202 and underlying mattress (not shown) to then protrude outwardly from mating side strap passage, e.g., 226, in the associated side 216 of the sheet 202 and underlying bed mattress. The distal, protruding end 228 of the securing strap 204 is then secured to side 216 of the sheet 202 such as by a hook and pile fastener sections matingly mounted between the protruding end 228 and the side 216 of the sheet 202. Other types of fasteners may also be used. Alternatively, the protruding end 228 may be lengthened and tied to adjacent structure (not shown) such a as a crib gate.

Figure 8:
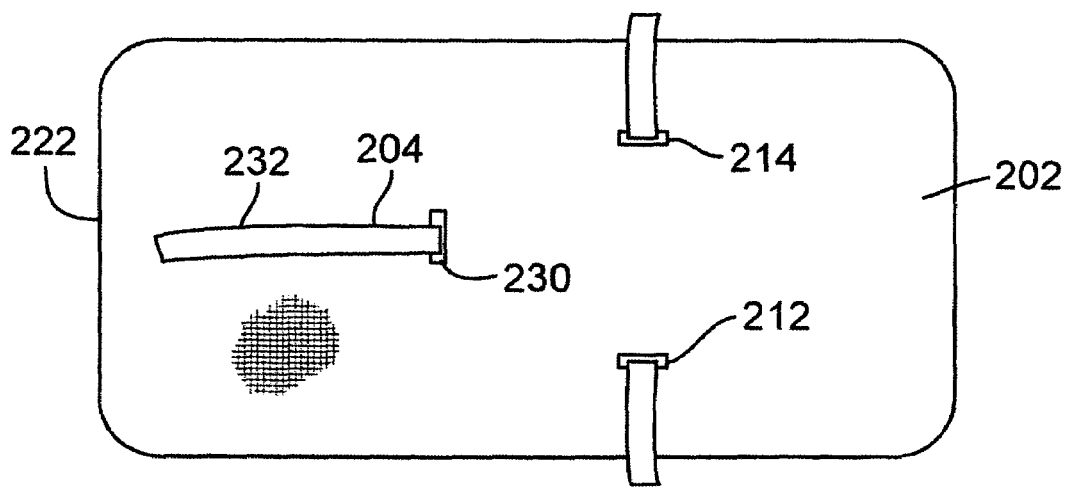
FIG. 8 shows a bottom view of the fitted sheet with the safety device mounted to the fitted sheet as in FIG. 7.

As shown in a somewhat alternative construction in FIG. 8, the axially extending strap 204 may be adjustable and/or removable rather than fixed to the bed sheet 202 as in FIG. 7 and, for example, extend through a mating strap passage 230 in the bed sheet 202. The fastening end 232 of the axially extending strap 204 may similarly be secured to the bed sheet 202 by hook and pile or other fasteners (not shown). Alternatively, the axially extending strap 204 may extend through yet an additional passage (not shown), such as in the bottom side 222 of the bed sheet 202 to be secured in the fashion of the opposing securing straps 206, 208 as shown in FIG. 7. Numerous other harness securing structures and techniques may be utilized.

For example, in yet another embodiment, the mating side strap passage 226 of FIG. 7 may be enlarged 240 as shown in FIG. 8. Further, the hook and pile fastener portion 242 secured to the bed sheet 202 may be widened to cover a greater lateral area on the side 216 of the bed sheet 202. This configuration can allow for lateral adjustment of the mounting or fastening position of the associated opposing or sidewardly extending securing strap 244. In this manner, the securing strap 244 may be mounted in various locations along the side 216 of the bed 202 and avoid interfering structure such as a crib gate or side bed post (not shown).

Figure 9:
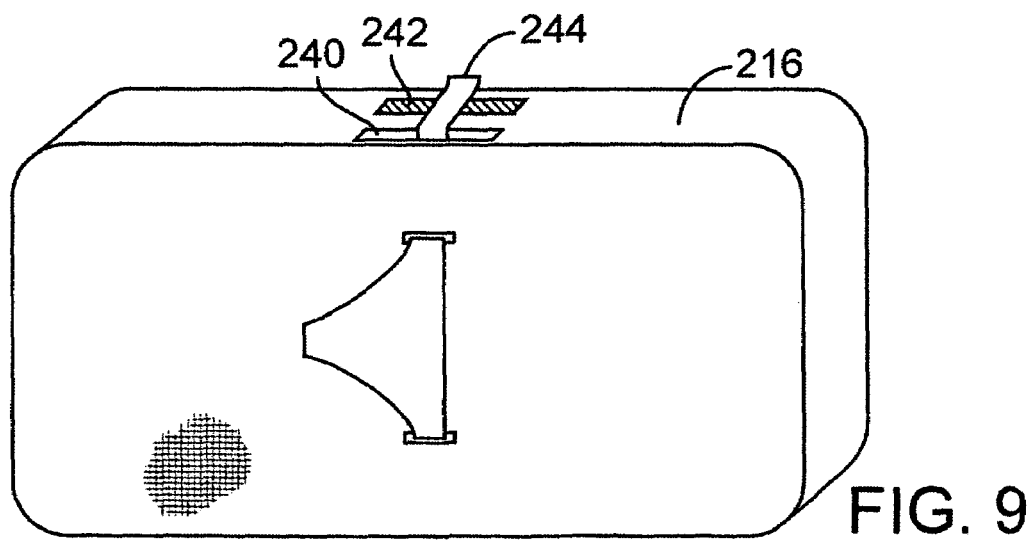
FIG. 9 shows a perspective view of an alternative arrangement for securing a safety device to a fitted mattress at the sides of the mattress.
Figure 10:
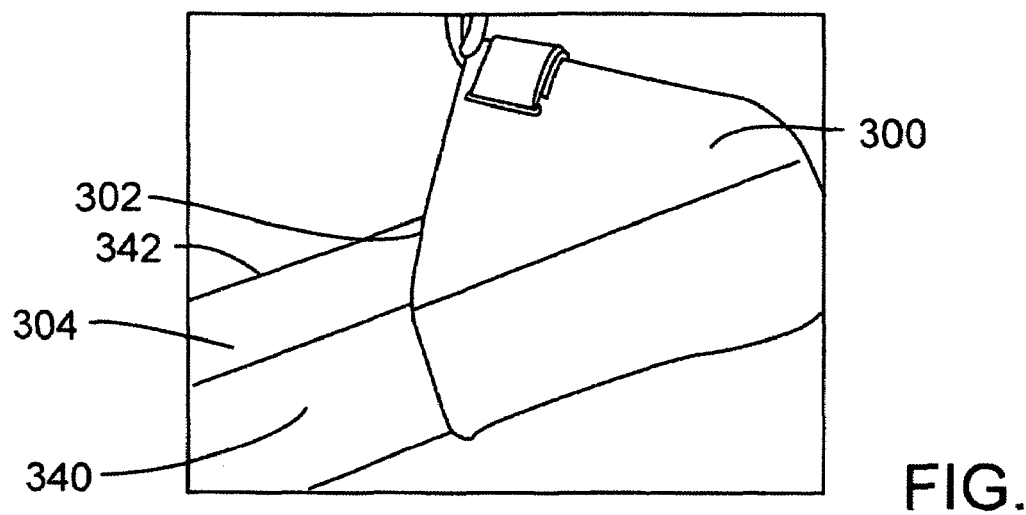
FIG. 10 is a side view showing a method in which a blanket is slid over the bottom end of a mattress with a cover sheet.
Figure 11:
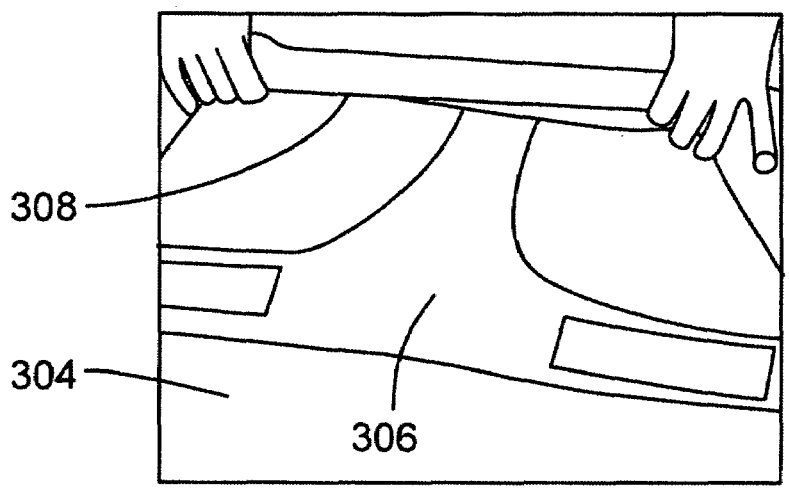
FIG. 11 is a perspective view showing insertion of a harness on top of the mattress, in the method of FIG. 10.
Figure 12:
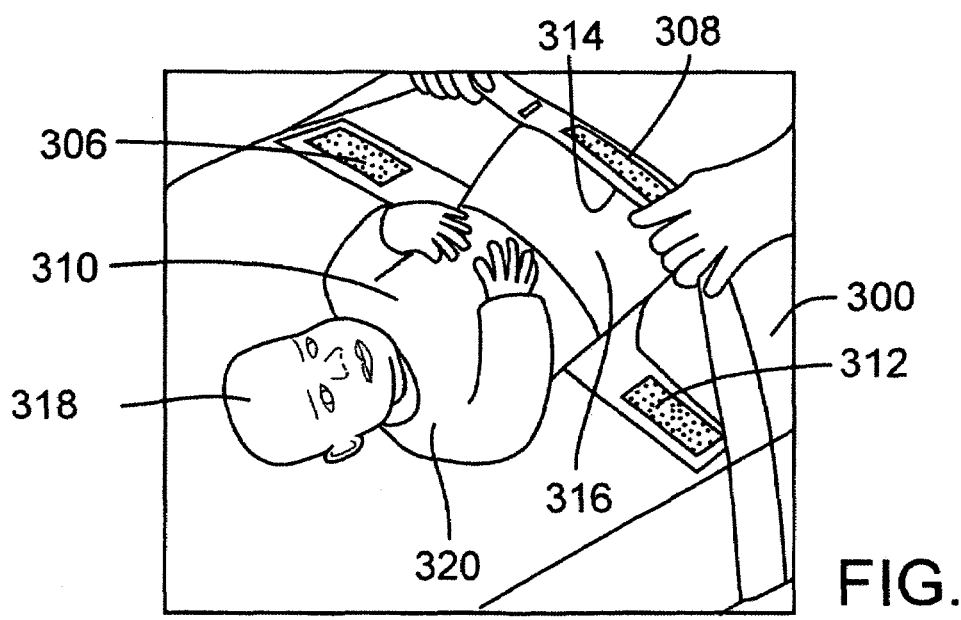
FIG. 12 is a perspective view showing insertion of an infant between the harness and upper blanket, in the method of FIG. 10.
Figure 13:
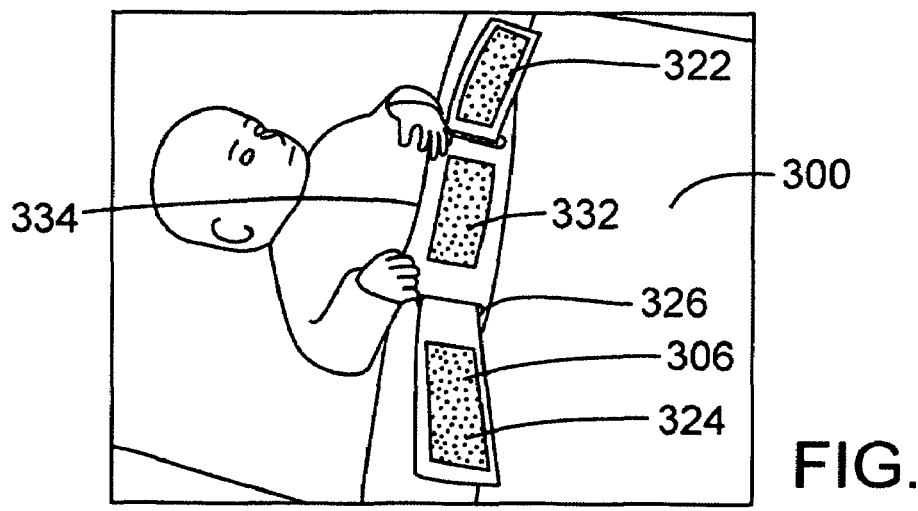
FIG. 13 is a perspective view showing the opposing securing straps of the harness pulled through mating strap passages in the blanket providing for strap locations on opposing sides of the infant's torso, in the method of FIG. 10.
Figure 14:
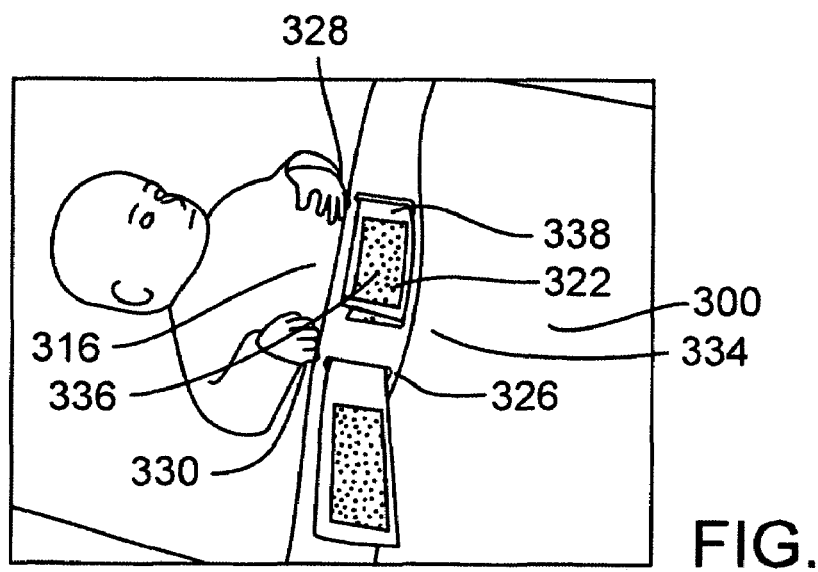
FIG. 14 is a perspective view showing a first securing strap secured to a mating hook and pile fastener section on the upper surface of the blanket above the infant's torso, in the method of FIG. 10.
Figure 15:
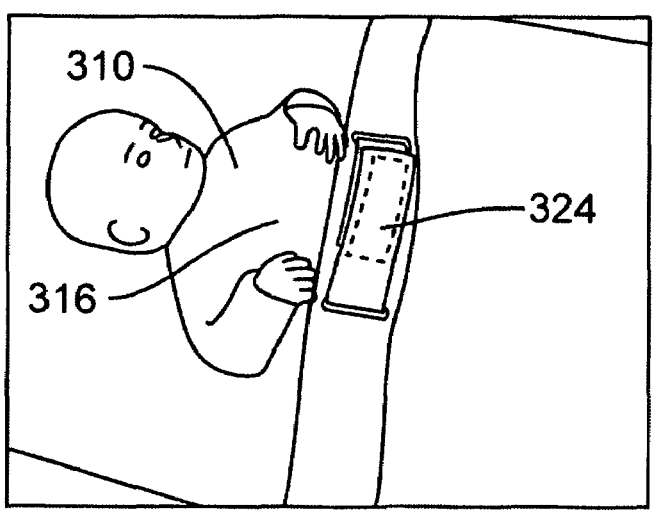
FIG. 15 is a perspective view showing a second securing strap secured to a mating hook and pile fastener section on the upper surface of the first secured strap above the infant's torso, completing the method of FIG. 10.

The securing harnesses shown in FIGS. 8 and 9 may thus be relatively easily removed from the associated bed sheet and replaced, washed, or repaired as desired. Further, they can be secured in position, to maintain an associated body in position, in a fashion that can be difficult or impossible for an infant, or perhaps other body, to undo the orientation of the harness when secured to the associated bed street or other structure.

In the embodiments of FIGS. 7–9, the harness is shown unattached to a sheet or blanket. A sheet (meaning herein any other desired cover, such as a blanket as noted above) may be either attached to the harness before or after installation of the harness and in any number of ways. For example, a sheet might be secured in position with respect the harness and associated infant or other body by securing corners of the sheet to a crib gate or other structure. The corners of the sheet may have any number of fastening devices attached to such or other locations. Examples can include straps secured to the sheet location, mating hook and pile fasteners mounted on the straps of mating structures, or button and mating passage fastening structures.

The sheet can be further secured in position in many other ways. One example is to secure the sheet to the harness above the infant or other body by means of mating hook and pile fastener sections mounted to the harness and the mating section of the sheet.

Alternatively, the sheet can include included pocket structure with the harness of FIGS. 7–9 mounted within the pocket to secure an infant or other body within the pocket. The pocket may be created by slip-over sheeting on a mattress, or it may be formed of a section of sheet stitched or otherwise fastened to another sheet.

With reference now to FIGS. 10–15, one method of utilizing a harness and associated sheet with an infant comprises:

A. sliding a pre-constructed or arranged pocket sheet 300 (such as, as one example, a stretchable fleece blanket in the embodiment of FIGS. 10–15) over the bottom or lower end 302 of a mattress pre-covered with an underlying fitted sheet 304;

B. inserting a somewhat triangularly shaped securing harness 306 between the fitted sheet 304 and mating upper section 308 of the pocket sheet 300;

C. placing an infant 310 on the upper face 312 of the harness 306 and below the mating upper section 308 of the pocket sheet 300, with the upper edge 314 of the mating upper section 308 of the pocket sheet 300 extending across the infant's torso 316 spaced from the infant's head 318 and, in this particular embodiment, shoulders 320;

D. pulling the two opposing securing straps 322, 324 of the harness 306 through mating strap passages, e.g., 326, in the sheet 300 providing for strap passage locations on opposing sides 328, 330 of the infant's torso 316;

E. securing a first securing strap 322 to a mating hook and pile fastener section 332 on the upper surface 334 of the sheet 300 above the infant's torso; and F. securing the opposing second securing strap 324 to a mating hook and pile fastener section 336 on the upper surface 338 of the first secured strap 322 above the infant's torso 316.

The infant 310 is thereby secured safely in position on the lower end 302 of the bed mattress generally equidistant from the opposing lateral sides 340, 342 of the bed mattress.

It can thus be seen that the applicants have provided body orienting device that may, depending on the embodiment utilized, relatively comfortably orient a body, such as a human body, with respect to other objects, particularly when the body is intended to be at rest. In this regard, the embodiments shown herein have shown particular structures for a harness. As noted above, other harness structures or configurations may be used to secure a body in position. For example, the harness may be enlarged to secure larger bodies, such as older children, infirm adults, or certain animals undergoing care.

In the embodiments such as those in which the securing element or harness is used in conjunction with a flexible, relatively thin, fleece sheet secured to a fitted or otherwise relatively secured bed sheet, such as in FIGS. 4, 5, and 10–15 for example:

reduces the risk of being kicked off or over the infant's head, thereby also reducing the risk of suffocation or breathing of oxygen reduced or depleted air;

reduces the risk that the baby may slip down under the blanket, further reducing the risk of overheating or suffocation;

reduces the need for excessive heating in the baby's room and further reducing the chance of overheating the baby;

allows comforting airflow around the baby as it kicks to maintain a desired body temperature;

positions the baby at the foot of the bed and away from the sides, thereby reducing danger of suffocation or breathing of oxygen reduced or depleted air;

maintains the baby in the correct sleeping position, comfortably, while reducing the danger sudden infant death syndrome;

maintains swaddling of the baby in the a soft harness, promoting increased sleep duration.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

For example, the harness may be configured to consist of a central body with three corners, and each corner may have extending sections that may wrap around a separate mounting strap and secure to the strap or to themselves by mating hook and pile fastening sections or other fastener devices. In turn, the harness may be mounted to one or more separate, removable, and adjustable mounting straps secured around or to a mounting structure, such as a bed. For example, two corners of the harness might be mounted to one strap extending across a bed, and another corner mounted to another strap extending across the bed.

It is to be understood that the foregoing is a detailed description of preferred and alternative embodiments. It would be apparent to those skilled in the art that many more modifications than mentioned above are possible without departing from the invention or while implementing it. The disclosure, therefore, is not to be restricted by the foregoing detailed descriptions, and the scope of the invention is to be determined by reference to the claims as issued.

We claim:

1. A body orienting device comprising in combination:

A. a body blanket sheet section having a body-facing surface, an opposing surface opposite the body-facing surface, and at least one securing element passage penetrating the body blanket sheet section;

B. a body securing harness having at least two opposing ends, with at least (i) a first of the opposing ends passable through the securing element passage and being adjustably securable with respect to the body blanket sheet section; and (ii) a second of the opposing ends being securable with respect to the body blanket sheet section, and (iii) a third end intermediate and distal from the two opposing ends, the third end being securable with respect to the body blanket sheet section;

whereby a body may be secured in position with respect to the body blanket sheet section by securing the body securing harness with respect to the body blanket sheet section.

2. The body orienting device of claim 1 wherein the body securing harness further comprises a generally triangular central section with the two opposing ends and the third end extending from the central section.

3. A body orienting device comprising in combination:

A. a sheet comprising a pocket section forming at least a portion of a pocket and having a body-facing surface, an opposing surface opposite the body-facing surface, and at least one securing element passage penetrating the sheet;

B. a body securing harness mountable adjacent the pocket section in the pocket and having at least two opposing ends, with at least (i) a first of the opposing ends passable through the securing element passage and being adjustably securable with respect to the sheet, a (ii) a second of the opposing ends being securable with respect to the sheet, the body securing harness also having a third end intermediate and distal from the two opposing ends and being securable with respect to the sheet;

whereby a body may be secured in position in the pocket with respect to the sheet by securing the body securing harness with respect to the sheet.

4. The body orienting device of claim 3 wherein the body securing harness comprises soft, flexible material.

5. The body orienting device of claim 3 wherein the body securing harness and the sheet comprise soft, flexible material.

6. The body orienting device of claim 5 wherein the pocket comprises resilient, stretchable material.

7. The body orienting device of claim 3 wherein (a) the sheet has at least four securing element passages, (b) the first of the opposing ends is passable through at least a first pair of securing element passages; and (ii) the second of the opposing ends is passable through at least a second pair of securing element passages.

8. A body orienting device comprising in combination:
A. a body blanket sheet section having a body-facing surface, an opposing surface opposite the body-facing surface, and at least a first and a second securing element passage penetrating the body blanket sheet section;
B. a flexible body securing element with a first securing end extending from the body securing element, a second securing end extending from the body securing element, and a third attachment end extending from the body securing element intermediate the first securing end and the second securing end, the first securing end being mountable in the first securing element passage and the second securing end being mountable in the second securing element passage.

9. The body orienting device of claim 8 wherein the first securing end is adjustably securable to the second securing end.

10. The body orienting device of claim 9 wherein the body blanket sheet section has an attachment element on the opposing surface and the first securing end is adjustably securable to the attachment element.

11. The body orienting device of claim 10 where the body blanket sheet section, attachment element, the first securing end, and the second securing end are comprised of relatively flexible and soft material.

12. The body orienting device of claim 8 wherein the body blanket sheet section has an attachment element on the opposing surface, the first securing end is adjustably securable to the attachment element, and the second securing end is securable with respect to the body blanket sheet section.

13. A body orienting device comprising in combination:
A. a sheet having a body-facing surface, an opposing surface opposite the body-facing surface, at least a first and a second securing element passage penetrating the sheet, and a pocket section forming at least a portion of a pocket;
B. a flexible body securing element with a first securing end extending from the body securing element, a second securing end extending from the body securing element, and a third attachment end extending from the body securing element intermediate the first securing end and the second securing end, the first securing end being mountable in the first securing element passage and the second securing end being mountable in the second securing element passage, said body securing element being mountable adjacent the pocket section in the pocket, whereby the body may be secured in position in the pocket.

14. The body orienting device of claim 13 wherein (a) the first securing end is adjustably securable to the second securing end, (b) the sheet has an attachment element on the opposing surface and the first securing end is adjustably securable to the attachment element, and (c) the body securing element is mountable adjacent the pocket section in the pocket, whereby the body may be secured in position in the pocket.

15. The body orienting device of claim 13 wherein the body securing element comprises soft material.

16. A method of securing a body in position with a flexible body securing element having a first securing end penetratingly mountable in a first passage in a body blanket sheet section, a second securing end penetratingly mountable in a second passage in a body blanket sheet section, and a third securing end distal from the first securing end and second securing end, the third securing end being securable with respect to the body blanket sheet section; the method comprising:
A. procuring the body securing element in a pre-oriented position with respect to the body blanket sheet section with at least the first securing element penetrating the first passage and placing the second element penetrating the second passage;
B. placing a body between the body securing element and the body blanket sheet section;
C. adjusting at least the first securing element with respect to the body and the body blanket sheet section, and securing the body with respect to the third securing end and an associated sheet section.

17. The body securing method of claim 16 wherein the body is an infant body.

18. A method of securing a body in position with a flexible body securing element having a first securing end penetratingly mountable in a first passage in a pocket in a body blanket sheet section and a second securing end penetratingly mountable in a second passage in a pocket in a body blanket sheet section, the method comprising:
A. positioning a body with respect to the pocket in the body blanket sheet section intermediate the first passage and second passage in the body blanket sheet section; and
B. securing the body securing element with respect to the pocket in the body blanket sheet section by securing at least the first securing element in a predetermined position penetrating the first passage and securing the second element in a predetermined position penetrating the second passage.

19. The body securing method of claim 18 wherein the body is an infant body.

20. A method of securing an infant in position with a flexible body securing harness having a first securing strap penetratingly mountable in a first passage in a sheet and a second securing strap penetratingly mountable in a second passage in a sheet, the method comprising:
A. arranging the harness in a sheet pocket comprising the sheet;
B. placing an infant face up on the harness within the sheet pocket;
C. pulling the first and second securing straps of the harness through mating strap passages in the sheet;
D. securing a first securing strap with respect to the infant; and E. securing the second sc curing strap with respect to the infant.

21. The infant securing method of claim 20 wherein the securing step (D) comprises securing the first securing strap to an external side of the sheet opposite the infant-facing side of the sheet and adjacent the infant's torso, and the securing step (E) comprises securing the second securing strap adjacent the external side of the sheet, the first securing strap, and the infant's torso.

22. The infant securing method of claim 21 wherein, upon completion of the method, the first and second passages in the sheet are on opposing sides of the infant's torso, and the upper sheet section of the sheet pocket is distal from the infant's face while containing at least a portion of the infant's torso.

\* \* \* \* \*